United States Patent [19]

Rance et al.

[11] 4,199,568

[45] Apr. 22, 1980

[54] TETRAPEPTIDE AMIDES

[75] Inventors: Michael J. Rance, Hessle; Balraj K. Handa, Wawne; Barry A. Morgan, Hessle, all of England

[73] Assignee: Reckitt & Colman Products Limited, London, England

[21] Appl. No.: 941,757

[22] Filed: Sep. 13, 1978

[30] Foreign Application Priority Data

Sep. 29, 1977 [GB]  United Kingdom ............... 40476/77

[51] Int. Cl.$^2$ ..................... A61K 37/00; C07C 103/52
[52] U.S. Cl. ............................... 424/177; 260/112.5 R
[58] Field of Search .................. 424/177; 260/112.5 R

[56] References Cited

PUBLICATIONS

Nature 268, 1977, pp. 547–549.

*Primary Examiner*—Delbert R. Phillips
*Attorney, Agent, or Firm*—Jesse B. Grove, Jr.

[57] ABSTRACT

Tetrapeptide amides of the formula

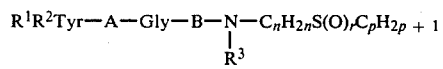

wherein $R^1$, $R^2$, $R^3$, A and B represent certain specified substituent groups and where n is 2–5, p is 1–5 and r is 1 or 2. The compounds exhibit pharmacological activity when tested in the transmurally stimulating guinea pig ileum preparation indicating their affinity for opiate receptor sites and they may therefore be used in man for those conditions where an opiate-like effect is indicated.

23 Claims, No Drawings

TETRAPEPTIDE AMIDES

This invention relates to peptides, to processes for their preparation and to therapeutic compositions thereof.

According to this invention there are provided compounds of the formula:

$$R^1R^2\text{Tyr}-A-\text{Gly}-B-\underset{\underset{R^3}{|}}{N}-C_nH_{2n}S(O)_rC_pH_{2p+1} \qquad \text{I}$$

wherein $R^1$ is hydrogen, alkyl $C_{1-4}$, alkenyl $C_{3-5}$, propargyl, cycloalkylmethyl $C_{4-8}$, or phenylalkyl $C_{1-3}$, $R^2$ is hydrogen or alkyl $C_{1-4}$;

A is a D-serine or D-threonine residue both optionally substituted on the $\beta$-OH by alkyl $C_{1-4}$, or a D-methionine, D-methionine sulphoxide or D-methionine sulphone residue or the group $-NH-CR^4H-CO-$ (where $R^4$ is alkyl $C_{1-5}$) the group having the D-configuration.

B is the group $-NR^6-CHR^8-CO-$ (where $R^6$ is hydrogen or alkyl $C_{1-4}$ and $R^8$ is $CH_2Ar$ where Ar is phenyl optionally substituted by chlorine, methyl, hydroxy or methoxy) the group having the L-configuration;

$R^3$ is hydrogen, alkyl $C_{1-10}$, phenyl or phenyl alkyl $C_{1-6}$; n is 2-5; p is 1-5; r is 1 or 2; and their acid addition salts.

Examples of A include D-alanine, D-leucine, D-isoleucine, D-norleucine, D-valine and D-norvaline.

Examples of B include L-phenylalanine, L-o-chlorophenylalanine, L-p-chlorophenylalanine, L-p-methoxyphenylalanine, L-p-methylphenylalanine and their N-alkyl $C_{1-4}$ derivatives such as for example L-N-methylphenylalanine.

In an aspect of the invention there are provided compounds of Formula I wherein $R^1$ is hydrogen, methyl, allyl, cyclopropylmethyl or phenethyl;

$R^2$ is hydrogen;

A is a D-serine, D-threonine, D-alanine, D-valine, D-norvaline, D-leucine, D-norleucine, D-o-methylserine, D-methionine, D-methionine sulphoxide or D-methionine sulphone residue or a residue of D-$\alpha$-aminobutyric acid;

B is a L-phenylalanine, L-N-methylphenylalanine or L-p-chlorophenylalanine residue;

$R^3$ is hydrogen, alkyl $C_{1-5}$ or phenylalkyl $C_{1-3}$;

n is 2 or 3; p is 1-3; r is 1 or 2; and their acid addition salts.

The symbols used herein for amino-acid derivatives are those customarily used in peptide chemistry such as are set out in Biochem. J. 126, 773 (1972). All amino-acid residues are of the natural or L-configuration unless specified otherwise.

The invention also provides therapeutic compositions comprising a compound of the formula, or a pharmaceutically acceptable acid addition salt thereof, in association with a pharmaceutically acceptable diluent or carrier.

The compounds of the invention exhibit pharmacological activity. Thus for example they have affinity for opiate receptor sites and as such may be useful as anagesics, narcotic antagonists or anti-diarrhoeal agents. The test used for the detection of their agonist activity at opiate receptor sites is that of employing the transmurally stimulated guinea pig ileum preparation described in Kosterlitz H. W., and Watt A. J., Brit. J. Pharmacol, and Chemotherapy 33, 266-176 (1968).

The compounds of the invention may be prepared by the standard methods of peptide chemistry.

Thus they may be produced by sequential coupling, usually from C-terminus, of suitably protected and activated amino-acids by either classical solution methods or solid phase procedures, or by coupling fragments consisting of suitably protected peptides.

Details concerning the selection of protecting groups and methods for their incorporation as well as suitable reaction conditions for forming amido (peptide) linkages and removal of protecting groups may be found in the following references:

(a) Houben Weyl; Methoden der Organischen Chemie Vol. 16 Parts I and II Synthese von Peptiden (Thieme 1974)

(b) Schroder & Lubke "The Peptides," Academic Press (1965)

The compounds of Formula I may be prepared from a compound of the formula $$H-M_2-W \qquad \text{II}$$

where $M_2$ is a protected amino acid or peptide residue and W is a group $NR^3C_nH_{2n}SC_pH_{2p+1}$ (wherein $R^3$, n and p are as hereinbefore defined) by either (a) coupling with a compound of the formula $$Y-M_1-OH \qquad \text{III}$$

where Y is a N-protecting group and $M_1$ is a protected amino acid or peptide residue (where $M_1$ and $M_2$ together represent $-\text{Tyr}-A-\text{Gly}-B-$ and when A and B are as hereinbefore defined), followed by the steps of oxidation and removal of the protection; or (b) oxidation, followed by coupling with a compound of formula $$Y-M_1-OH$$

where Y and $M_1$ are as defined above, followed by removal of the protection.

It has been found in practice that in (a) it is more convenient to remove the protection before carrying out the oxidation.

The couplings may be achieved by the standard methods of peptide synthesis, either with or without isolation of the activated component corresponding to the compound of formula III.

Oxidations are usually accomplished in a suitable solvent with 3-4 molar equivalents of oxidising agent. In practice it has been found that concentrations of sulphide of ~20 mM afford compounds of formula I in which r=1 (sulphinyl compounds) whereas higher concentrations ~200 mM affords mainly compounds of formula I in which r=2 (sulphonyl compounds). Conveniently the oxidations are carried out employing hydrogen peroxide in for example ethanol.

The invention is illustrated by the following nonlimiting Examples in which temperatures are in degrees centigrade.

The following abbreviations are used throughout

BOC: t-Butyloxycarbonyl

Bu$^t$: t-Butyl

IBCF: Isobutylchloroformate

Z: Benzyloxycarbonyl

ONSu: N-Hydroxysuccinimido

DCCI: Dicyclohexylcarbodiimide

DCU: Dicyclohexylurea

HONSu: N-Hydroxysuccinimide

NMM: N-Methylmorpholine

DMF: Dimethylformamide

DCHA: Dicyclohexylamine

DME: 1,2-Dimethoxyethane

Tmp: 3-methylthiopropyl

Tos: Tosylate

TMG: Tetramethylguanidine

The various compounds and intermediates were examined by thin layer chromatography (t.l.c.) on silica gel Kieselgel GF 254 plates using the following systems:

| 1F | methanol, chloroform | 1:9 |
|---|---|---|
| 1G | methanol, chloroform | 1:19 |
| 2B | chloroform, methanol, acetic acid | 19:9:1 |
| 2D | chloroform, methanol, acetic acid | 30:5:1 |
| 3A | chloroform, methanol, acetic acid, water | 60:18:2:3 |
| 3B | chloroform, methanol, acetic acid, water | 30:20:4:6 |
| 3C | chloroform, methanol, acetic acid, water | 90:27:2:3 |
| 4A | n-Butanol, ethyl acetate, acetic acid, water | 1:1:1:1 |
| 7B | Ethyl acetate, pyridine, acetic acid, water | 60:20:6:11 |
| 7C | Ethyl acetate, pyridine, acetic acid, water | 120:20:6:11 |
| 7D | Ethyl acetate, pyridine, acetic acid, water | 240:20:6:11 |
| 7E | Ethyl acetate, pyridine, acetic acid, water | 360:20:6:11 |
| 7G | Ethyl acetate, pyridine, acetic acid, water | 960:20:6:11 |
| 28B | Ethyl acetate, petroleum ether 40°-60° | 10:1 |
| 32A | Ethyl acetate, i-propanol | 9:1 |
| 32B | Ethyl acetate, i-propanol | 19:1 |

EXAMPLE 1

L-Tyrosyl-D-alanyl-glycyl-N-methyl-L-phenylalanine-3-methylsulphinylpropylamide hydrochloride This was prepared according to the following method.

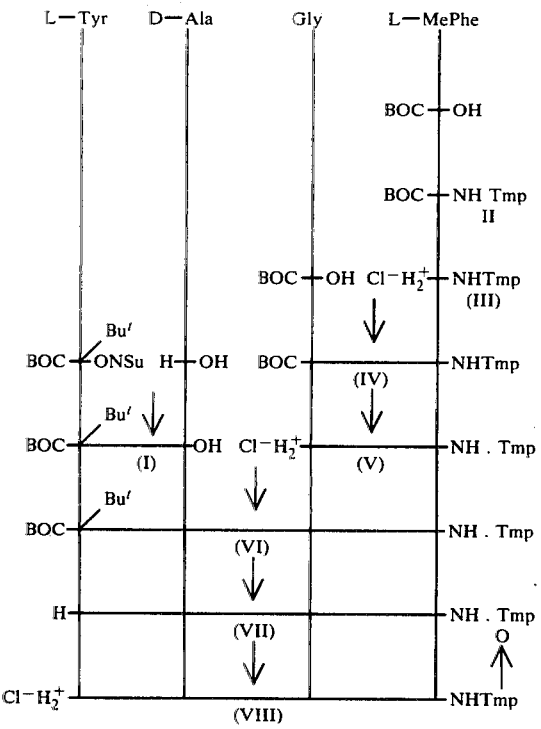

(a) N-t-Butyloxycarbonyl-O-t-butyl-L-tyrosyl-D-alanine (I)

BOC-Tyr(Bu$^t$)-OH (2.5 g) was dissolved in DME, cooled in an ice-salt bath and then HONSu (0.853 g) and DCCI (1.53 g) were added. The reaction mixture was allowed to attain room temperature and stirred overnight. DCU was filtered off and the solvent evaporated. The residue was dissolved in DMF (5 ml) and added at room temperature to a solution of D-Alanine (0.66 g) in DMF (5 ml) and water (1 ml) in the presence of TMG (0.86 g). The reaction mixture was stirred overnight, the solvent was evaporated, and the residue treated with water (100 ml). The aqueous solution was extracted with ethyl acetate (2×50 ml) and acidified to pH 4 with 10% citric acid. The mixture was extracted with ethyl acetate (2×100 ml) and the combined organic extracts washed with water until free of acid, and dried (Na$_2$SO$_4$). On evaporation of this solvent a gum was obtained which crystallised from ethyl acetate to give the dipeptide derivative (I) (1.3 g, 43%) m.p. 186°-187°, Rf7C=0.65; Rf8A=0.25.

(b) N-t Butyloxycarbonyl-N-methyl-L-phenylalanine-3-methylthiopropyl amide (II)

BOC-MePhe-OH (1 g) was dissolved in dichloromethane (10 ml) and cooled at −20° when isobutylchloroformate (0.5 g) and NMM (0.37 g) were added. After 2 minutes, Tmp.NH$_2$HCl (0.51 g) and NMM (0.37 g) were added and the reaction mixture allowed to warm up to room temperature. After stirring for 3 hours the solvent was evaporated and the residue partioned between ethylacetate (100 ml) and water (50 ml). The organic layer was washed with a saturated solution of sodium bicarbonate (2×50 ml), 10% citric acid solution (3×50 ml) and with water until free of acid and then with a saturated brine solution. The organic phase was dried over Na₂SO₄ and evaporated to yield (II) as an oil (1.3 g) Rf32A=0.75 Rf7G=0.8

(c)
N-t-Butyloxycarbonylglycyl-N-methyl-L-phenylalanine-3-methylthiopropylamide (IV)

(i) BOC-MePhe-NHTmp (1.3 g) was treated, at room temperature with excess 3.5 M HCl in ethylacetate (3 ml) for 40 minutes. The solvent was evaporated and the residue triturated with diethyl ether at 0°. A hygroscopic solid was obtained which was filtered and dried over P₂O₅ under high vacuum to yield III (1 g.) Rf7C=0.25

(ii) BOC-Gly-OH (0.69 g) was dissolved in dichloromethane (10 ml) and cooled at −20°. Isobutylchloroformate (0.53 g) and NMM (0.4 g) were added with stirring. After 2 minutes Cl⁻H₂⁺MePhe-NHTmp (1.2 g) and NMM (0.4 g) were added and the reaction mixture was allowed to attain room temperature. The stirring was continued for additional 3 hours when the reaction was worked up as described for (II). The dipeptide amide (IV) was obtained as a gum.
Yield=(1.25 g)
Rf32A=0.7, Rf7G=0.75

(d)
N-t-Butyloxycarbonyl-O-t-butyl-L-tyrosyl-D-alanyl-glycyl-N-methyl-L-phenylalanine-3-methylthiopropylamide (VI)

(i) BOC-Gly-MePhe-NHTmp (1.2 g) was treated at ambient temperature with 3.5 M hydrogen chloride in ethyl acetate (5 ml) for 45 minutes and then the solvent was evaporated. The residue was triturated with ether and the hydrochloride (V) was obtained as a hygroscopic solid. It was dried over P₂O₅ under high vacuum.
Yield=1 g (98%)
Rf7C=0.2

(ii) BOC-Tyr(Buᵗ)-D-Ala-OH (0.67 g) and Cl⁻H₂⁺Gly-MePhe-NHTmp (0.59 g) were dissolved in DMF (5 ml) and cooled in an ice-salt bath when HONSu (0.415 g) and DCCI (0.338 g) were added followed by NMM (0.166 g, 1.66 ml of 10% solution in DMF). The reaction mixture was allowed to attain room temperature and stirred for 18 hours and the DCU filtered off and the solvent evaporated. The residue was dissolved in ethylacetate (150 ml) washed with saturated solution of sodium bicarbonate (3×50 ml), 10% citric acid solution (3×50 ml) and with water until neutral and then with a saturated brine solution. The organic phase was dried (Na₂SO₄) and evaporated to yield (VI) as a semi-solid gum
Rf7G=0.65

(e)
L-Tyrosyl-D-alanyl-glycyl-N-methyl-L-phenylalanine-3-methylthiopropylamide (VII)

BOC-Tyr(Buᵗ)-D-Ala-Gly-MePhe-NHTmp (0.95 g) was treated at ambient temperature with 3.5 M hydrogen chloride in ethyl acetate (5 ml) for 45 minutes and then the solvent was evaporated. The residue was chromatographed on a silica gel column (60 cm×2.5 cm) with solvent system 7C. Appropriate fractions were pooled, evaporated, and the residue lyophillised from water to yield VII. (yield=0.45 g) Rf7C=0.25, Rf3A=0.45

(f)
L-Tyrosyl-D-alanyl-glycyl-N-methyl-L-phenylalanine-3-methylsulphinylpropylamide hydrochloride (VIII)

H-Tyr-D-Ala-Gly-MePhe-NH-Tmp (0.1 g) was dissolved in ethanol 5 ml) and treated at room temperature with hydrogen peroxide (0.25 ml of 20 volumes). After 2 hours the solvent was evaporated and the residue chromatographed on a silica gel column (45 cm×2.5 cm) with solvent system 3C. Appropriate fractions were pooled, evaporated and the residue lyophillised in 0.1 M HCl (10 ml) to yield VIII as a white solid (0.045 g).
Rf3A=0.13, Rf3B=0.62, Rf7B=0.16 [α]=14.8° (C=0.25, 0.1 M HCl)

EXAMPLE 2

N-Methyl-L-tyrosyl-D-alanyl-glycyl-N-methyl-L-phenylalanine-3-methylsulphinylpropylamide hydrochloride This was prepared according to the following method:

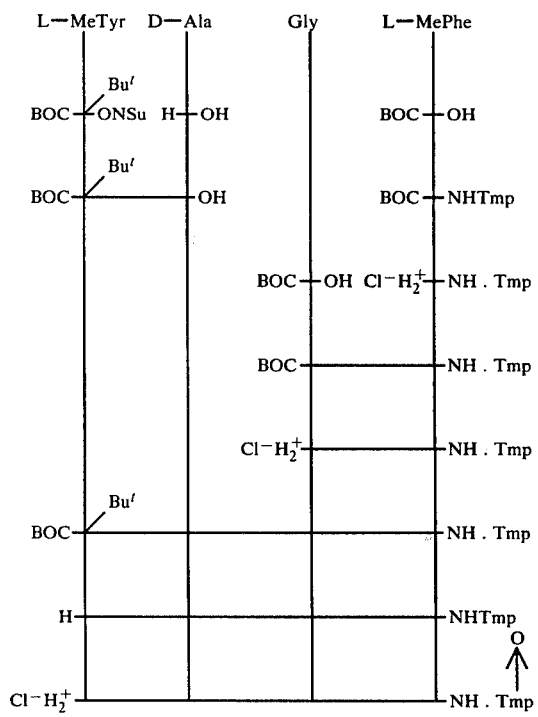

(a) N-Methyl-N-t-butyloxycarbonyl O-t-butyl-L-tyrosyl-D-alanine

This dipeptide was prepared (by the method of Example 1(a)) by converting N-Me-N-BOC-Tyr(Buᵗ)-OH (2.5 g) to its ONSu active ester and then coupling to D-Alanine (0.731 g) in the presence of TMG (0.954 g). The dipeptide was recrystallised from ethyl acetate/petroleum ether, yield=2 g, m.p. 109°-110°, Rf7D=0.50

(b) N-Methyl-N-t-butyloxycarbonyl-O-t-butyl-L-tyrosyl-D-alanyl-glycyl-N-methyl-L-phenylalanine-3-methylthiopropylamide This was prepared (by the method of Example 1(d)(ii)) by coupling N-Me-N-BOC-Tyr(Bu$^t$)-D-Ala-OH (0.634 g) with Cl$^-$H$_2^+$.Gly-MePhe-NHTmp (0.54 g) in DMF (5 ml) using HONSU (0.38 g) and DCCI (0.31 g) in the presence of NMM (0.152 g; 1.52 ml of a 10% solution in DMF). After the the work up a gum was obtained which solidified under high vacuum.
Yield=0.75 g (c) N-Methyl-L-tyrosyl-D-alanyl-glycyl-N-methyl-L-phenylalanine-3-methylthiopropylamide N-Me-N-Boc-Tyr(Bu$^t$)-D-Ala-Gly-MePhe-NH Tmp (0.75 g) was treated at ambient temperature with excess 3.5 M hydrogen chloride in ethyl acetate for 40 minutes and then the solvent was evaporated. The residue was chromatographed on a silica gel column (60 cm×2.5 cm) with solvent system 7C. The appropriate fractions were pooled, evaporated, and the residue lyophillised in 0.1 M HCl (15 ml) to yield the title compound as a white solid (0.35 g) Rf7B=0.4; Rf3A=0.45

(d) N-Methyl-L-tyrosyl-D-alanyl-glycyl-N-methyl-L-phenylalanine-3-methylsulphinylpropylamide hydrochloride N-Me-Tyr-D-Ala-Gly-MePhe-NHTmp (0.1 g) was dissolved in ethanol (50 ml) and treated, at room temperature, with hydrogen peroxide (0.25 ml of 20 volumes). After 2 hours the solvent was evaporated and the residue chromatographed on a silica gel column (45 cm×2.5 cm) with solvent system 3C. The appropriate fractions were pooled, evaporated and the residue lyophillized in 0.1 M HCl (10 ml) to yield the title compound as a white solid (0.035 g). Rf3A=0.15, Rf3B 0.64, Rf7B 0.16, $[\alpha]_D^{24}$=19.1°(C=0.26 in 0.1 M HCl)

EXAMPLE 3

N-Methyl-L-tyrosyl-D-alanylglycyl-L-phenylalanine-3-methylsulphinylpropylamide hydrochloride This was prepared according to the following method (a) N-t-Butyloxycarbonyl-L-phenylalanine-3-thiomethylpropylamide This was prepared from BOC-PheOH and 3-methylthiopropylamide by the method of Example 1(b) the product was obtained as an oil (b) N-Methyl-l-Tyrosyl-D-alanylglycyl-L-phenylalanine-3-methylsulphinylpropylamide hydrochloride This was prepared by deprotecting the above protected amide and coupling with BOC Gly OH by the method of Example 1(c). The resulting dipeptide derivative was deprotected and coupled with BOC MeTyr(-Bu$^t$)D-Ala OH by the method of Example 1(d) and the resulting tetrapeptide deprotected and oxidised by the methods of Examples 1(e) and 1(f).

The resulting compound was lyophillised from 0.1 M HCl to yield a white solid
Rf3A=0.11, Rf3B=0.54, Rf7B=0.16.$[\alpha]_D^{24}$=35.8 (C=0.25, 0.1 M HCl)

EXAMPLE 4

L-Tyrosyl-D-sergylglycyl-N-methyl-L-phenylalanine-3-methylsulphinylpropylamide (a) N-t-Butyloxycarbonyl-O-t-butyl-L-tyrosyl-D-serine D-serine (0.95 g, 9 mM) was dissolved in 4 M NaOH (1.5 ml). Water (4 ml) was added followed by solid sodium bicarbonate (0.504 g, 6 mM) to give a clear solution. A solution of BOC Tyr (Bu$^t$) ONSu (3.48 g, 8 mM) in DMF (4 ml) was then added and the mixture stirred for 48 hours at 22°. The solvent was then evaporated and the residue dissolved in water (80 ml). The aqueous solution was adjusted to pH 3 with concentrated aqueous citric acid and extracted with EtOAc (2×50 ml). The combined EtOAc extracts were washed until neutral, dried and then evaporated to ~10 ml. Cyclohexane (50 ml) was added and the turbid solution left at 5° for 48 hours. The resulting solid was collected by filtration and dried under vacuum to yield the desired dipeptide (2.16 g, 64%) as white crystals m.p. 158.5°–160°

(b) N-t-Butyloxycarbonyl-O-t-butyl-L-tyrosyl-D-serylglycyl-N-methyl-L-phenylalanine-3-methylthiopropylamide This was prepared by coupling BOC Tyr (Bu$^t$)-D-SerOH with Cl$^\ominus$H$_2^\oplus$GlyMePheNHTmp by the method of Example 1(d)

(c) L-Tyrosyl-D-Serylglycyl-N-methyl-L-phenylalanine-3-methylsulphinylpropylamide This was prepared from the above protected pentapeptide by deprotection and oxidation by the method of Examples 1(e) and 1(f). The desired sulphinyl compound was lyophilised from water to yield a white solid.
Rf3A=0.10, Rf3B=0.47, Rf7B=0.15

EXAMPLE 5

L-Tyrosyl-D-methionyl(sulphoxide)glycyl-N-methyl-L-phenylalanine-3-methylsulphinylpropylamide N-t-Butyloxycarbonyl-O-t-butyl-L-tyrosyl-D-methionine This dipeptide was prepared by coupling BOC Tyr (Bu$^t$) ONSu with D-methionine sodium salt by the method of Example 4(a). The product was obtained as a glassy solid. Rf3A=0.69, Rf32A=0.33. m.p. 229.5°–230°

The material was homogenous on t.l.c.

(b) N-t-Butyloxycarbonyl-O-t-butyl-L-tyrosyl-D-methionylglycyl-N-methyl-L-phenylalanine-3-methylthiopropylamide This was prepared by coupling the dipeptide prepared in Example 5(a) with Cl$^\ominus$$^\oplus$H$_2$Gly Me Phe NH Tmp by the method of Example 1(d). After chromatography on silica gel the product was isolated as a colourless glass which was homogenous on t.l.c. Rf7G=0.4, Rf28B=0.24

(c)
L-Tyrosyl-D-methionylglycyl-N-methyl-L-phenylalanine-3-methylthio propylamide This was prepared by deprotecting the material prepared in 5(b) by the method of Example 1(e). The purified tetrapeptide amide was homogenous on t.l.c. Rf2B=0.67, Rf2D=0.24 Rf3B=0.69

(d)
L-Tyrosyl-D-methionyl(sulphoxide)-N-methyl-L-phenylalanine-3-methylsulphinylpropylamide This was prepared by oxidation of the corresponding bis-sulphide by the method of Example 1(f). The purified bis-sulphoxide was homogenous on t.l.c.
Rf3B=0.59. Rf4A=0.53 Rf7B=0.075 $[\alpha]_D^{24}=20.4$ (C=0.525, 0.1 M HCl)

EXAMPLE 6
L-Tyrosyl-D-norvalylglycyl-N-methyl-L-phenylalanine-3-methylsulphinylpropylamide

(a)
N-t-Butoxycarbonyl-C-t-butyl-L-tyrosyl-D-norvaline

Boc-Tyr(Bu$^t$)-ONSu(3.27 g) was dissolved in DMF (3 ml). TMG (0.867 g) and D-norvaline (0.996 g) were dissolved in DMF (10 ml). The two solutions were mixed and allowed to stir at 22° for four days.

The solvent was removed by evaporation and the residue partitioned between ethyl acetate (60 ml) and water (40 ml). The mixture was acidified to pH 3. The phases were separated and the aqueous phase extracted with ethylacetate (3×20 ml). The combined organic extracts were washed with water until neutral, and dried over Na$_2$SO$_4$.

The dipeptide was obtained as a colourless oil (2.02 g, 61.4% yield) by evaporating the solvent. The material was homogenous on t.l.c. Rf2B=0.62, Rf28B=0.19 Rf32B=0.29

(b)
N-t-Butyloxycarbonyl-O-t-butyl-L-tyrosyl-D-norvalylglycyl-N-methyl-L-phenylalanine-3-methylthiopropylamide This was prepared by coupling the dipeptide prepared in 6(a) with Cl$^\ominus\oplus$H$_2$Gly Me Phe NH Tmp by the method of Example 1(d). After chromatography on silica the product was isolated as a colourless glass which was homogeneous on t.l.c. Rf7G=0.44, Rf28B=0.27

(c)
L-Tyrosyl-D-norvalyglycyl-N-methyl-L-phenylalanine-3-methylthiopropylamide This was prepared by deprotecting the material prepared in 6(b), by the method of Example 1(e). After chromatography on silica the tetrapeptide amide was homogeneous on t.l.c. Rf2B=0.46, Rf2D=0.23 Rf3B=0.69

(d)
L-Tyrosyl-D-norvalylglycyl-N-methyl-L-phenylalanine-3-methylsulphinylpropylamide This was prepared by oxidation of the corresponding sulphide 6(c) by the method of Example 1(f). The purified sulphoxide was homogenous on t.l.c. Rf3B=0.63 Rf4A=0.67, Rf7B=0.18 $[\alpha]_D^{24}=24.8$ (C=0.49, 0.1 M HCl)

EXAMPLE 7
L-Tyrosyl-D-alanylglycyl-N-methyl-L-phenylalanine 2-methylsulphinylethylamide This was prepared according to the following method

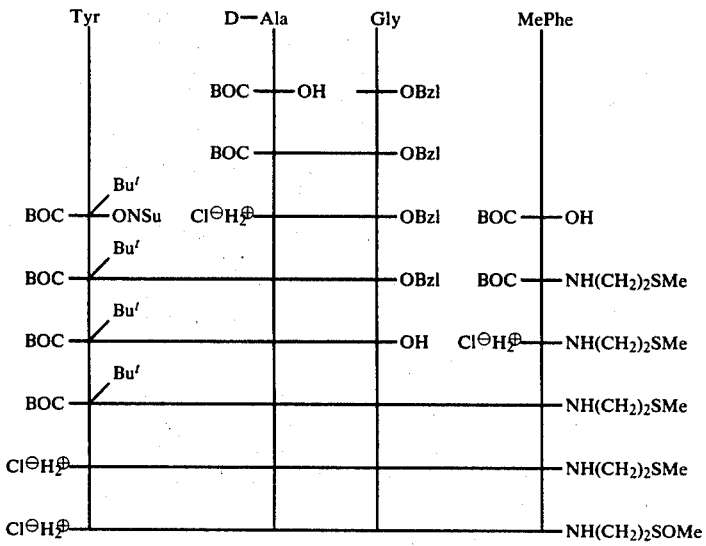

(a) t-Butyloxycarbonyl-N-methyl-L-phenylalanine 2-methylthioethylamide

This was prepared by coupling of BOC Me Phe OH with 2-methylthioethylamine by the method of Example 1(b) The product was obtained as an oil. Rf1G=0.71 Rf32A=0.48

(b) N-methyl-L-phenylanine 2-methylthioethylamide trifluoroacetate

BOC Me Phe NH(CH$_2$)$_2$SMe (410 mg) was dissolved in water/trifluoroacetic acid (1:9, 5 ml) and the solution stirred for 1 hour. The solution was then evaporated, re-evaporated from water, ethanol and finally triturated with ether to yield the desired trifluoroacetate salt as a sticky solid. Rf3A=0.65, Rf4A=0.67; Rf7C=0.38 The product was used without further purification.

(c) N-t-Butyloxycarbonyl-O-t-butyl-L-tyrosyl-D-alanylglycyl-N-methyl-L-phenylalanine-2-methylthioethylamide BOC Tyr (Bu$^t$) D-Ala Gly OH (542 mg, 1.16 mM) was dissolved in DMF (2 ml) and CH$_2$Cl$_2$ (8 ml) and the solution cooled to −20°. IBCF was then added (160 mg, 1.16 mM) followed by NMM (118 mg, 1.16 mM). After 2 minutes a solution of $\oplus$HMePhe NH(CH$_2$)$_2$SMe TFA$\ominus$ (from 1.16 mM of the corresponding BOC derivative) in CH$_2$Cl$_2$ (5 ml) and NMM (118 mg, 1.16 mM) was added and the stirred mixture allowed to attain room temperature. After 48 hours the solution was partitioned between Et OAc and aqueous NaHCO$_3$. The EtOAc layer was extracted with aqueous NaHCO$_3$ (×2), 10% aqueous citric acid (×3) dried and evaporated. The residue was purified by chromatography on silica gel (30×2.5 cm). Elution with IPA/EtOAc (1:19) gave the pure tetrapeptide amide as a clear gum which was homogenous on the t.l.c. Rf1G=0.41, Rf7C=0.73, Rf32B=0.29

(d) L-Tyrosyl-D-alanylglycyl-N-methyl-L-phenylalanine 2-methylthioethylamide

The protected tetrapeptide 7(c) was deblocked by the method of Example 1(e). The crude product was purified by chromatography on silica in solvent system 3A to give a gum. Rf3A=0.44, Rf4A=0.68, Rf7C=0.19

(e) L-Tyrosyl-D-alanylglycyl-N-methyl-L-phenylalanine 2-methylsulphinylethylamide The sulphide of Example 7(d) was oxidised by the method of Example 1(f). The crude product was purified by ion-exchange chromatography on carboxylmethyl cellulose. The column (30×1.5 cm) was initially equilibrated with 0.05% aqueous pyridine and eluted with a gradient to 1% pyridine 1% acetic acid. The eluant was analysed by t.l.c. and appropriate fractions pooled and evaporated. The residue was lyophillised from water to yield the desired peptide sulphoxide as its acetate salt. Rf3A=0.17, Rf4A=0.53, Rf7B=0.10 [α]$_{589}^{20}$ 21.6° (C=1, 0.1 N HCl)

EXAMPLE 8

L-Tyrosyl-D-alanylglycyl-N-methyl-L-phenylalanine-N-methyl-3-methylsulphinyl propyl amide This was prepared according to the following method (a) N-Methyl-3-methylthiopropanamide 3-Methylthiopropionic acid chloride (2.08 g) was added to a solution of methylamine (5 ml, 7.8 M) in dry ether at 0°. The white precipitate was removed by filtration and the filtrate evaporated. A gum was obtained which crystallised on standing. Yield=1.8 g (90%)

(b) N-Methyl-3-methylthiopropylamine

This was prepared by reduction of N-methyl-3-methylthiopropanamide as described for the preparation of 10(b). The product was a gum. Rf3A=0.44

(c) t-Butyloxycarbonyl-N-methyl-L-phenylalanine-N-methyl-3-methylthiopropylamide This was prepared by coupling BOCMePheOH with N-methyl-3-methylthiopropylamine by the method of Example 1(b). The pure product was obtained after silica gel column chromatography in ethylacetate/cyclohexane (1:3). Rf=0.52 (ethylacetate:cyclohexane, 1:1)

(d) N-Methyl-L-phenylalanine-N-methyl-3-methylthiopropylamide hydrochloride

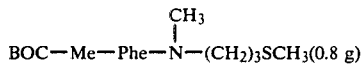

BOC—Me—Phe—N—(CH$_2$)$_3$SCH$_3$(0.8 g)

was dissolved in 3 M HCl/ethylacetate (6 ml) and stirred at room temperature for 40 minutes when the solvent was evaporated. The residue was triturated with dry ether to yield a hydroscopic solid.
Yield=0.500 g. Rf3A=0.8

(e) N-t-Butyloxycarbonyl-O-t-butyl-L-tyrosyl-D-alanylglycyl-N-methyl-L-phenylalanine-N-methyl-3-methylthiopropylamide N-Methylphenylalanine-N-methyl-3-methylpropylamide hydrochloride (8d)(0.5 g) was coupled with BOC Tyr (Bu$^t$) D-Ala Gly OH (0.736 g) as described for Example 7(c). The coupled product was obtained as a yellow solid. Yield 0.76 g, Rf1G=0.48

(f) L-Tyrosyl-D-alanylglycyl-N-methyl-L-phenylalanine-N-methyl-3-methylthiopropylamide The protected peptide 8(e) (0.75 g) was deblocked in 90% TFA as described for 7(b). The trifluoroacetate salt was obtained as a solid which was purified by silica gel column chromatography using the solvent system 3A. An amorphous solid was obtained on lyophilisation.
Yield=0.525 g. Rf3A=0.45, Rf3B=0.92, Rf7B=0.43

(g) L-Tyrosyl-D-alanylglycyl-N-methyl-L-phenylalanine-N-methyl-3-methylsulphinypropylamide The sulphide of Example 8(f) was oxidised by the method of Example 1(b). The crude product was purified by ion-exchange chromatography on carboxymethyl Sephadex as described in Example 7(e). The sulphinyl compound was obtained as an amorphous solid as its acetate salt.
Rf3A=0.22, Rf3B=0.64, Rf7B=0.43 [α]$_D^{24}$=−8.6°(C=0.5, 0.1 M HCl)

EXAMPLE 9

L-Tyrosyl-D-alanylglycyl-N-methyl-L-phenylalanine 2-propylsulphinylethylamide (a) t-Butyloxycarbonyl-N-methyl-L-phenylalanine 2-propylthioethylamide This was prepared from BOC Me Phe OH and 2-propylthioethylamide by the method of Example 1(b). The acid (1.39 g) and 2-propylthioethylamine (650 mg)

gave 1.5 g of product as a gum. Rf32B=0.61, Rf3A=0.87

(b) N-Methyl-L-phenylalanine 2-propylthioethylamide trifluoracetate

The protected amide from (a)(1.4 g) was deprotected with aqueous trifluoroacetic acid (10 ml) as in Example 7(b). Chromatography on silica in chloroform:methanol:acetic acid: water 120:36:2:3 gave a gum (1.1 g). Rf3A=0.61, Rf7B=0.71

(c) N-t-Butoxycarbonyl-O-t-butyl-L-tyrosyl-D-alanylglycyl-N-methyl-L-phenylalanine 2-propylthioethylamide By the method described in Example 7(c), the above trifluoroacetate salt (1.0 g) and BOC Tyr (Bu$^t$) D Ala Gly OH (1.16 g) gave the tetrapeptide amide as a gum which was not further purified Rf3A=0.75, Rf32A=0.5

(d) L-Tyrosyl-D-alanylglycyl-N-methyl-L-phenylalanine 2-propylthioethylamide

Deprotection of the product from (c) by the method of Example 7(b) gave 505 mg of the tetrapeptide amide after chromatography on silica in chloroform:methanol:acetic acid:water 120:36:2:3. Rf3A=0.46

(e) L-Tyrosyl-D-alanylglycyl-N-methyl-L-phenylalanine 2-propylsulphinylethylamide The product from (d) was oxidised by the method of Example 1(f). Chromatography on carboxymethyl Sephadex resin in a gradient from 0.05% pyridine in water to 2% pyridine, 2% acetic acid in water gave the sulphoxide.
Rf3A=0.32, Rf4A=0.65, Rf7B=0.20
$[\alpha]_D^{24}$=20.2 (C=0.98, 0.1 M HCl)

EXAMPLE 10

L-Tyrosyl-D-alanylglycyl-N-methyl-L-phenylalanine N-isoamyl-N-3-methylsulphinylpropylamide (a) 3-Methylthiopropan-N-isoamylamide 3-Methylthiopropionyl chloride (2.08 g) in diethyl ether (30 ml) was added slowly to a stirred solution of isoamylamine (2.94 g). After 15 minutes the mixture was extracted twice with water, and the ether layer then washed with citric acid solution and then with water. Drying and evaporation gave the amide as a gum (2.8 g) Rf1F=0.63, Rf7E=0.79, Rf32A=0.49

(b) iso Amyl 3-methylthiopropylamine

The amide from (a) (1.9 g) in tetrahydrofuran (20 ml) was treated under nitrogen at 0° with boranetetrahydrofuran complex (1 Molar in tetrahydrofuran 20 ml) and stirred overnight. 2 Molar hydrogen chloride in methanol (20 ml) was added and the mixture was boiled for 30 minutes, evaporated and the residue partitioned between ethyl acetate and water. The aqueous layer was basified and extracted with ether. The dried extract was evaporated to give the amine an oil (1.6 g). Rf3A=0.72, Rf7B=0.63, Rf4A=0.74

(c) t-Butoxycarbonyl-N-methyl-L-phenylalanine N-isoamyl-N-3-methylthiopropylamide This was prepared from BOC Me Phe OH and isoamyl 3-methylthiopropylamine (525 mg) by the method of Example 1(b). After chromatography on silica in ethylacetate-isopropanol 95:5 the product was obtained as an oil which crystallised on standing (987 mg). Rf1G=0.71

(d) N-Methyl-L-phenylalanine N-isoamyl-N-3-methylthiopropylamide trifluoroacetate This was prepared by the method of Example 7(b) and obtained as a gum Rf3A=0.91, Rf7C=0.35

(e) N-t-Butoxycarbonyl-O-t-butyl-L-tyrosyl-D-alanylglycyl-N-methyl-L-phenylalanine N-isoamyl-N-3-methylthiopropylamide N-Methylphenylalanine N-isoamyl-N-3-methylthiopropylamide trifluoroacetate (d from 900 mg of protected material) was coupled with BOC Tyr (Bu$^t$) D-Ala Gly OH (960 mg) by the method used in Example 7(c). Chromatography on silica in ethyl acetate-isopropanol (95:5) gave a gum (653 mg). Rf32A=0.56, Rf1G=0.52.

(f) L-Tyrosyl-D-alanylglycyl-N-methyl-L-phenylalanine N-isoamyl-N-3-methylthiopropylamide trifluoroacetate The protected peptide amide from (e) (580 mg) was deprotected by the method used in Example 7(b). Chromatography on silica in chloroform-methanol-acetic acid-water (120-36-2-3) gave the product (311 mg). Rf3A=0.55, Rf7C=0.28, Rf4A=0.56

(g) L-Tyrosyl-D-alanylglycyl-N-methyl-L-phenylalanine N-isoamyl-N-3-methylsulphinylpropylamide Oxidation of the methylthiopropylamide (280 mg) from (f) by the method used in Example 1(f) and purification by chromatography on carboxymethyl Sephadex resin (pyridinium form) in 0.05% pyridine, followed by a gradient to 1% pyridine, 1% acetic acid, yielded a product which was lyophillised from water and gave the acetate salt (189 mg).
Rf3A=0.29, Rf4A=0.58, Rf7B=0.26, $[\alpha]_{589}^{23}$ 7.7° (C=0.9 in 0.1 M HCl)

EXAMPLE 11

L-Tyrosyl-D-alanylglycyl-N-methyl-L-phenylalanine N-3-methylsulphinylpropyl-N-2-phenylethylamide (a) 3-Methylthiopropan-N-2-phenylethylamide Prepared from 3-methylthiopropionyl chloride (2.76 g) and 2-phenylethylamine (5.04 g) by the method used in Example 10(a). The solid product (3.79 g) was pure by t.l.c. A sample crystallised from aqueous methanol as needles m.p. 56°-59°.

(b) N-3-Methylthiopropyl-N-2-phenylethylamine

Reduction of 3-methylthiopropan-N-2-phenylethylamide (2.23 g) by the method of Example 10(b) gave the amine (1.4 g) as an oil. Rf7C=0.29, Rf4A=0.69, Rf3A=0.51

(c) N-t-Butoxycarbonyl-N-methyl-L-phenylalanine N-3-methylthiopropyl-N-2-phenylethylamide The amine from (b) (627 mg) was coupled with BOC Me Phe OH (from 1.38 g dicyclohexylamine salt) by the method of Example 1(b). The product (1.39 g) was an oil. Rf3A=0.89, Rf32A=0.68,

(d) N-Methyl-L-phenylalanine N-3-methylthiopropyl-N-2-phenylethylamide trifluoroacetate The protected amide from (c) (622 mg) was treated with trifluoroacetic acid as in Example 7(b). The amine salt was obtained as a gum. Rf3A=0.73, Rf4A=0.72, Rf7C=0.46

(e) N-t-Butoxycarbonyl-C-t-butyl-L-tyrosyl-D-alanylglycyl-N-methyl-L-phenylalanine N-3-methylthiopropyl-N-2-phenylethylamide This was prepared from the amine salt from (d) and BOC Tyr (Bu$^t$) D Ala Gly CH (615 mg) by the method of Example 7(c). After chromatography on silica in solvent 32B it was obtained as a gum (491 mg). Rf1G=0.45 Rf32A=0.53

(f) L-Tyrosyl-D-alanylglycyl-N-methyl-L-phenylalanine N-3-methylthiopropyl-N-2-phenylethylamide trifluoroacetate The protected amide from (e) (400 mg) was deprotected with aqueous trifluoroacetic acid by the method of Example 7(b) and gave the solid title compound (290 mg). Rf3A=0.54, Rf4A=0.79, Rf7C=0.19

(g) L-Tyrosyl-D-alanylglycyl-N-methyl-L-phenylalanine N-3-methylsulphinylpropyl-N-2-phenylethylamide L-Tyrosyl-D-alanylglycyl-N-methyl-L-phenylalanine N-3-methylthiopropyl-N-2-phenylethylamide (260 mg) was oxidised by the procedure of Example 1(f). Purification by ion exchange chromatography on carboxymethyl cellulose resin in a gradient from 0.05% pyridine to 1% pyridine, 1% acetic acid gave the required sulphoxide (176 mg). Rf3A=0.31, Rf4A=0.57, Rf7B=0.23, $[\alpha]_{589}^{20}$ −13.9° (C=1 in 0.1 M HCl)

EXAMPLE 12

L-Tyrosyl-D-alanylglycyl-N-methyl-L-phenylalanine-2-methylsulphonylpropylamide hydrochloride This was prepared by oxidation of the corresponding sulphide (Example 1e). Tyr D-Ala Gly MePhe NH(CH$_2$)$_3$SMe (110 mg) was dissolved in ethanol (5 ml) and treated at room temperature with hydrogen peroxide (0.25 ml of 20 volumes). After stirring for two hours the solvent was evaporated and the residue chromatographed on silica gel column (45 cm×2.5 cm) with solvent system 3C. The desired sulphone was eluted before the corresponding sulphoxide. The fractions were analysed by t.l.c. (system 3A) and those containing the pure sulphone pooled, evaporated and the residue lyophillised from 0.1 M HCl to yield Tyr D-Ala Gly Me Phe NH(CH$_2$)$_3$S(O$_2$)CH$_3$ (30 mg) as a white solid. Rf3A=0.15, Rf3B=0.67, Rf7B=0.25. $[\alpha]_D^{24}$=13.3 (C=0.27 in 0.1 M HCl)

EXAMPLE 13

N-Methyl-L-Tyrosyl-D-alanylglycyl-N-methyl-L-phenylalanine 3-methylsulphonylpropylamide hydrochloride This was prepared by oxidation of the corresponding sulphide (Example 2c) by the method of Example 12. Me Tyr D-Ala Gly Me Phe NH(CH$_2$)$_3$SO$_2$CH$_3$ was obtained as a white solid Rf3A=0.16, Rf3B=0.53, Rf7B=0.21

EXAMPLE 14

L-Tyrosyl-D-alanylglycyl-L-phenylalanine-3-methylsulphonylpropylamide hydrochloride This was prepared by oxidation of L-tyrosyl-D-alanylglycylphenylalanine-3-methylthiopropylamide by the method of Example 12. Tyr D-Ala Gly Phe NH(CH$_2$)$_3$SO$_2$Me was obtained as a white solid Rf3A=0.13, Rf3B=0.59, Rf7B=0.25, $[\alpha]_D^{24}$=38.5 (C=0.25 in 0.1 M HCl).

The Table sets out details of further compounds of Formula I which may be prepared by the methods of the above Examples or by other techniques well known in peptide chemistry.

TABLE

Allyl-Tyr-D-Ala-Gly-MePhe-NH(CH$_2$)$_3$SOMe
Cpm-Tyr-D-Ala-Gly-MePhe-NH(CH$_2$)$_3$SOMe
H-Tyr-D-Ala-Gly-Phe-NH(CH$_2$)$_3$SOMe
Allyl-Tyr-D-Ala-Gly-Phe-NH(CH$_2$)$_3$SOMe
Cpm-Tyr-D-Ala-Gly-Phe-NH(CH$_2$)$_3$SOMe
Ph(CH$_2$)$_2$Tyr-D-Ala-Gly-MePhe-NH(CH$_2$)$_3$SOMe
H-Tyr-D-Met-Gly-MePhe-NH(CH$_2$)$_3$SOMe
Allyl-Tyr-D-Met-Gly-MePhe-NH(CH$_2$)$_3$SOMe
Allyl-Tyr-D-Ser-Gly-MePhe-NH(CH$_2$)$_3$SOMe
H-Tyr-D-Ala-Gly-MePhe(p-Cl)-NH(CH$_2$)$_3$SOMe
Allyl-Tyr-D-Ala-Gly-MePhe-NH(CH$_2$)$_2$SOMe
H-Tyr-D-Ala-Gly-MePhe-NH(CH$_2$)$_4$SOMe
Allyl-Tyr-D-Ala-Gly-MePhe-NH(CH$_2$)$_4$SOMe
Me-Tyr-D-Met(O)-Gly-MePhe-NH(CH$_2$)$_3$SOMe
H-Tyr-D-Ala-Gly-Phe-NH(CH$_2$)$_3$SO$_2$Me
H-Tyr-D-Thr-Gly-MePhe-NH(CH$_2$)$_3$SOMe
H-Tyr-D-Val-Gly-MePhe-NH(CH$_2$)$_3$SOMe
H-Tyr-D-Leu-Gly-MePhe-NH(CH$_2$)$_3$SOMe
H-Tyr-D-Nle-Gly-MePhe-NH(CH$_2$)$_3$SOMe
H-Tyr-D-Ser(OMe)-Gly-MePhe-NH(CH$_2$)$_3$SOMe
H-Tyr-D-Met(O$_2$)-Gly-MePhe-NH(CH$_2$)$_3$SOMe
H-Tyr-D-Abu-Gly-MePhe-NH(CH$_2$)$_3$SOMe
H-Tyr-D-Ala-Gly-Phe(p-Cl)-NH(CH$_2$)$_3$SOMe
Me-Tyr-D-Ala-Gly-Phe(p-Cl)-NH(CH$_2$)$_3$SOMe In the above mentioned test method of Kosterlitz and Watt male or female guinea pigs (Duncan Hartley strain) are killed by a blow on the head and a portion of the ileum removed and set up in an isolated organ bath of 50 ml volume. A 'twitch' response is produced by low frequency (0.1 Hz) stimulation with 0.5 msec rectilinear pulses. The response is depressed by a large number of different pharmacologically active agents (local anaesthetics, smooth muscle depressants, presynaptic α-receptor stimulants, and narcotic agonists).

A test compound is dissolved in distilled water to produce a stock solution of concentration 1 mg/ml. Serial dilutions are carried out using Krebs solution to product concentrations of 10 ug, 1 ug and 0.1 ug/ml. The compound is tested by adding between 0.1–0.3 ml of the solutions to the organ bath. A dose response curve is then drawn and compared with that for Met-enkephaline.

In this test Me-Tyr-D-Ala-Gly-MePhe-NH(CH$_2$)$_3$SOMe possessed approximately fifteen times the activity of Met-enkephaline and H-Tyr-D-Ala-Gly-MePhe-NH(CH$_2$)$_3$SOMe was approximately eleven times. The compounds were also evaluated in the mouse phenylquinone induced writhing test of Hendershot L.

C. and Forsaith J., J. Pharm. Exp. Therap. 125, 237 (1959); when administered i.v. they had ED$_{50}$'s of respectively 0.004 and 0.0045 mg/Kg.

The therapeutic compositions may be in a form suitable for oral administration or in a form suitable for parenteral administration. Such oral compositions may take the form of capsules, tablets, granules or liquid preparations such as elixirs, syrups or suspensions.

Compositions intended for parenteral administration may be in the form of sterile preparations such as solutions in water or saline.

For the purposes of convenience of accuracy of dosing the compositions are advantageously employed in a unit dosage form.

What is claimed is:

1. A compound of the formula:

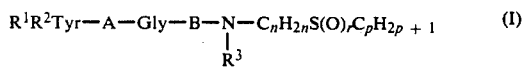

wherein
R$^1$ is hydrogen, alkyl C$_{1-4}$, alkenyl C$_{3-5}$, propargyl, cycloalkylmethyl C$_{4-8}$, or phenylalkyl C$_{1-3}$;
R$^2$ is hydrogen or alkyl C$_{1-4}$;
A is a D-serine or D-threonine residue both optionally substituted on the β-OH by alkyl C$_{1-4}$, or a D-methionine, D-methionine sulphoxide or D-methionine sulphone residue or the group —NH—CR$^4$H—CO— (where R$^4$ is alkyl C$_{1-5}$) the group having the D-configuration;
B is the group —NR$^6$—CHR$^8$—CO— (where R$^6$ is hydrogen or alkyl C$_{1-4}$ and R$^8$ is CH$_2$Ar where Ar is phenyl optionally substituted by chlorine, methyl, hydroxy or methoxy) the group having the L-configuration;
R$^3$ is hydrogen, alkyl C$_{1-10}$, phenyl or phenyl alkyl C$_{1-6}$; n is 2-5; p is 1-5; r is 1 or 2; and their acid addition salts.

2. A compound as claimed in claim 1 wherein
R$^1$ is hydrogen, methyl, allyl, cyclopropylmethyl or phenethyl;
R$^2$ is hydrogen;
A is a D-serine, D-threonine, D-alanine, D-valine, D-norvaline, D-leucine, D-norleucine, D-O-methylserine, D-methionine, D-methionine sulphoxide or D-methionine sulphone residue or a residue of D-α-aminobutyric acid; B is a L-phenylalanine, L-N-methylphenylalanine or L-p-chlorophenylalanine residue;
R$^3$ is hydrogen, alkyl C$_{1-5}$ or phenylalkyl C$_{1-3}$;
n is 2 or 3; p is 1-3; r is 1 or 2; and their acid addition salts.

3. A compound of claim 1 which is L-tyrosyl-D-alanylglycyl-N-methyl-L-phenylalanine-3-methylsulphinylpropylamide or an acid addition salt thereof.

4. A compound of claim 1 which is N-methyl-L-tyrosyl-D-alanylglycyl-N-methyl-L-phenylalanine-3-methylsulphinylpropylamide or an acid addition salt thereof.

5. A compound of claim 1 which is N-methyl-L-tyrosyl-D-alanylglycyl-L-phenylalanine-3-methylsulphinylpropylamide or an acid addition salt thereof.

6. A compound of claim 1 which is L-tyrosyl-D-serylglycyl-N-methyl-L-phenylalanine-3-methylsulphinylpropylamide or an acid addition salt thereof.

7. A compound of claim 1 which is L-tyrosyl-D-methionine(sulphoxide)glycyl-N-methyl-L-phenylalanine-3-methylsulphinylpropylamide or an acid addition salt thereof.

8. A compound of claim 1 which is L-tyrosyl-D-norvalylglycyl-N-methyl-L-phenylalanine-3-methylsulphinylpropylamide or an acid addition salt thereof.

9. A compound of claim 1 which is L-tyrosyl-D-alanylglycyl-N-methyl-L-phenylalanine-2-methylsulphinylethylamide or an acid addition salt thereof.

10. A compound of claim 1 which is L-tyrosyl-D-alanylglycyl-N-methyl-L-phenylalanine-N-methyl-3-methylsulphinylpropylamide or an acid addition salt thereof.

11. A compound of claim 1 which is L-tyrosyl-D-alanylglycyl-N-methyl-L-phenylalanine-2-propylsulphinylethylamide or an acid addition salt thereof.

12. A compound of claim 1 which is L-tyrosyl-D-alanylglycyl-N-methyl-L-phenylalanine-N-isoamyl-N-3-methylsulphinylpropylamide or an acid addition salt thereof.

13. A compound of claim 1 which is L-tyrosyl-D-alanylglycyl-N-methyl-L-phenylalanine-N-3-methylsulphinylpropyl-N-2-phenylethylamide or an acid addition salt thereof.

14. A compound of claim 1 which is L-tyrosyl-D-alanylglycyl-N-methyl-L-phenylalanine-3-methylsulphonylpropylamide or an acid addition salt thereof.

15. A compound of claim 1 which is N-methyl-L-tyrosyl-D-alanylglycyl-N-methyl-L-phenylalanine-3-methylsulphonylpropylamide or an acid addition salt thereof.

16. A compound of claim 1 which is L-tyrosyl-D-alanylglycyl-L-phenylalanine-3-methylsulphonylpropylamide or an acid addition salt thereof.

17. A compound of claim 1 which is L-tyrosyl-D-methionylglycyl-N-methyl-L-phenylalanine-3-methylsulphinylpropylamide or an acid addition salt thereof.

18. A compound of claim 1 which is L-tyrosyl-D-alanylglycyl-N-methyl-L-p-chlorophenylalanine-3-methyl-sulphinylpropylamide or an acid addition salt thereof.

19. A compound of claim 1 which is L-tyrosyl-D-alanylglycyl-N-methyl-L-phenylalanine-4-methylsulphinylbutylamide or an acid addition salt thereof.

20. A compound of claim 1 which is N-methyl-L-tyrosyl-D-methionine(sulphoxide)glycyl-N-methyl-L-phenylalanine-3-methylsulphinylpropylamide or an acid addition salt thereof.

21. A compound of claim 1 which is L-tyrosine-D-alanylglycyl-L-phenylalanine-3-methylsulphinyl-propylamide or an acid addition salt thereof.

22. A pharmaceutical composition which comprises an effective amount of at least one compound as claimed in claim 1 or a pharmaceutically acceptable salt thereof together with a pharmaceutically acceptable diluent or carrier.

23. A compound of the formula:

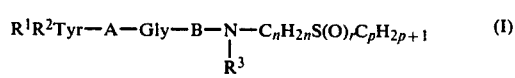

wherein
R$^1$ is hydrogen, alkyl C$_{1-4}$, alkenyl C$_{3-5}$, propargyl, cycloalkylmethyl C$_{4-8}$, or phenylalkyl C$_{1-3}$;
R$^2$ is hydrogen or alkyl C$_{1-4}$;
A is a D-serine or D-threonine residue both optionally substituted on the β-OH by alkyl C$_{1-4}$, or a D-methionine, D-methionine sulphoxide or D- methionine sulphone residue or the group —NH—CR$^4$H—CO— (where R$^4$ is alkyl C$_{1-5}$) the group having the D-configuration;

B is a L-phenylalanine or L-N-methylphenylalanine residue;

R$^3$ is hydrogen, alkyl C$_{1-10}$, phenyl or phenyl alkyl C$_{1-6}$; n is 2–5; p is 1–5; r is 1 or 2; and their acid addition salts.

* * * * *